US008680323B2

(12) United States Patent
Bock et al.

(10) Patent No.: US 8,680,323 B2

(45) Date of Patent: Mar. 25, 2014

(54) PROCESS FOR PREPARING ISOCYANATES BY THERMAL DISSOCIATION OF CARBAMATES

(75) Inventors: Michael Bock, Ruppertsberg (DE); Axel Franzke, Mannheim (DE); Robert Baumann, Mannheim (DE); Eckhard Stroefer, Mannheim (DE)

(73) Assignee: BASF SE, Ludwigshafen (DE)

( * ) Notice: Subject to any disclaimer, the term of this patent is extended or adjusted under 35 U.S.C. 154(b) by 302 days.

(21) Appl. No.: 13/008,457

(22) Filed: Jan. 18, 2011

(65) Prior Publication Data

US 2011/0178329 A1 Jul. 21, 2011

Related U.S. Application Data

(60) Provisional application No. 61/296,050, filed on Jan. 19, 2010.

(51) Int. Cl.
*C07C 263/04* (2006.01)

(52) U.S. Cl.
USPC .......................................... 560/345; 560/338

(58) Field of Classification Search
USPC .................................................. 560/345, 338
See application file for complete search history.

(56) References Cited

U.S. PATENT DOCUMENTS

| | | | | |
|---|---|---|---|---|
| 4,348,540 | A * | 9/1982 | Ferris et al. | 568/472 |
| 5,883,291 | A * | 3/1999 | Schleenstein et al. | 560/345 |
| 6,559,346 | B1 * | 5/2003 | Therre et al. | 568/483 |
| 7,100,905 | B2 * | 9/2006 | Weinle et al. | 261/77 |
| 7,282,119 | B2 * | 10/2007 | Odedra et al. | 203/29 |
| 8,053,595 | B2 * | 11/2011 | Shinohata et al. | 560/345 |
| 2010/0331564 | A1 | 12/2010 | Leitner et al. | |
| 2011/0004012 | A1 | 1/2011 | Leitner et al. | |
| 2011/0015424 | A1 | 1/2011 | Leitner et al. | |
| 2011/0137067 | A1 | 6/2011 | Franzke et al. | |

FOREIGN PATENT DOCUMENTS

| | | | |
|---|---|---|---|
| DE | 199 07 648 | A1 | 8/2000 |
| EP | 0 092 738 | A1 | 11/1983 |
| EP | 0 555 628 | A2 | 8/1993 |
| EP | 0 795 543 | A1 | 9/1997 |
| EP | 1 493 475 | B1 | 6/2007 |
| WO | WO 2009/115538 | A1 | 9/2009 |
| WO | WO 2009/115539 | A1 | 9/2009 |
| WO | WO 2009/121786 | A1 | 10/2009 |
| WO | WO 2010/057909 | A1 | 5/2010 |
| WO | WO 2011/015541 | A1 | 2/2011 |
| WO | WO 2011/036062 | A2 | 3/2011 |
| WO | WO 2011/051314 | A1 | 5/2011 |
| WO | WO 2011/067242 | A1 | 6/2011 |

OTHER PUBLICATIONS

U.S. Appl. No. 13/125,895, filed Apr. 25, 2011, Geissler, et al.

J. H. Saunders, et al., "Polyurethanes: Chemistry and Technology", Interscience Publishers, 1962, Table 10, p. 146.

U.S. Appl. No. 13/163,928, filed Jun. 20, 2011, Rosendahl, et al.

U.S. Appl. No. 13/394,647, filed Mar. 7, 2012, Mattke, et al.

U.S. Appl. No. 13/502,763, filed Apr. 19, 2012, Bock, et al.

U.S. Appl. No. 13/479,961, filed May 24, 2012, Stroefer, et al.

U.S. Appl. No. 13/513,460, filed Jun. 1, 2012, Bock, et al.

* cited by examiner

*Primary Examiner* — Johann R Richter
*Assistant Examiner* — Pancham Bakshi
(74) *Attorney, Agent, or Firm* — Oblon, Spivak, McClelland, Maier & Neustadt, L.L.P.

(57) ABSTRACT

The invention relates to a process for preparing isocyanates by thermal dissociation of carbamates and separation by distillation of the reaction mixture from the carbamate dissociation, comprising the corresponding isocyanate and the corresponding alcohol, by distillation in a column (K) having an enrichment section (V) and a stripping section (A), where the carbamate (1) is introduced between the enrichment section (V) and the stripping section (A) and the isocyanate is taken off as a constituent of the bottom stream (2) and the alcohol is taken off as a constituent of the overhead stream (3) from the column (K), in the presence of an inert solvent, wherein an intermediate boiler having a boiling point between the boiling point of the isocyanate and the boiling point of the alcohol under the operating conditions of the carbamate dissociation is used as inert solvent and is fed as external runback (4) in liquid form in a purity of >95% by weight, based on the total weight of the external runback (4), in the upper region of the enrichment section (V) and as gaseous, superheated stream (5) into the lower region of stripping section (A) at one or more points.

16 Claims, 1 Drawing Sheet

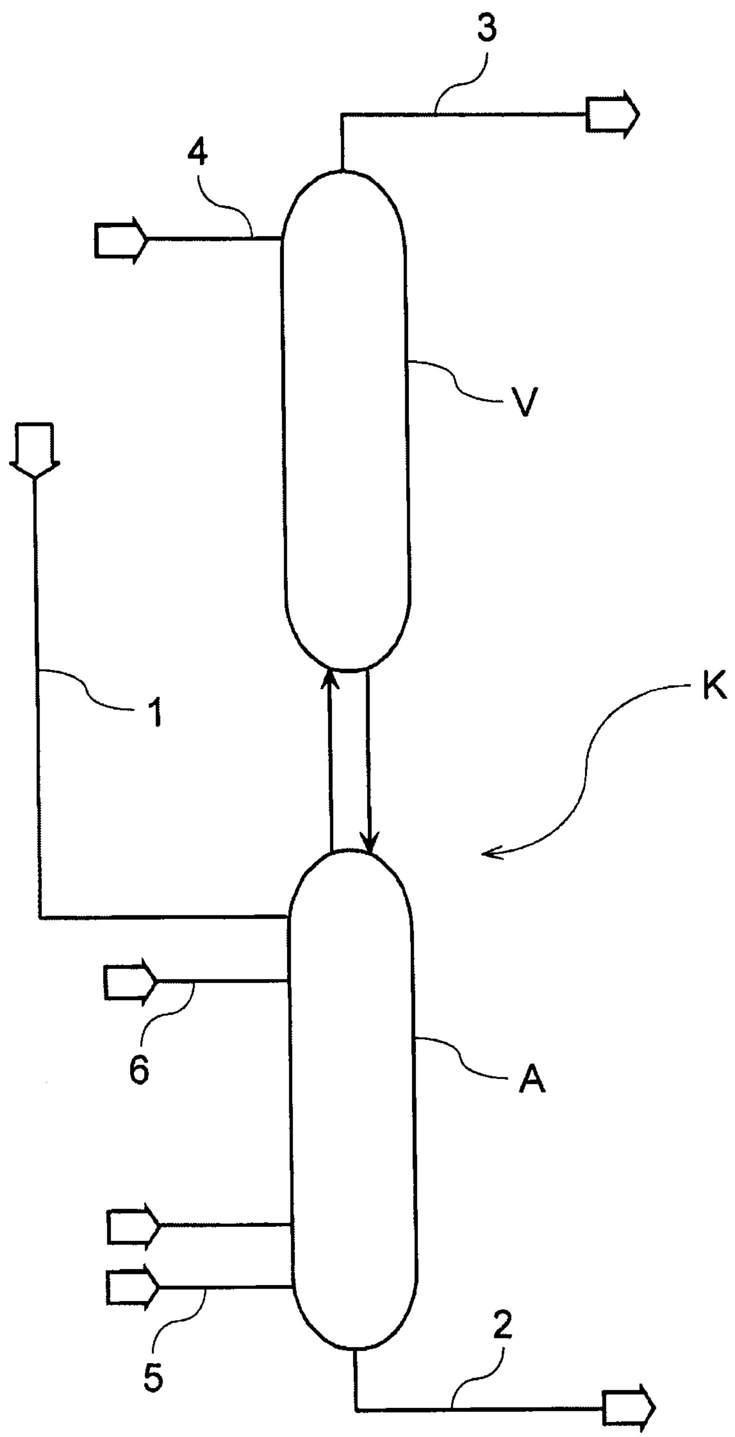
3
4
V
1
K
6
A
5
2

PROCESS FOR PREPARING ISOCYANATES BY THERMAL DISSOCIATION OF CARBAMATES

This patent application claims the benefit of U.S. provisional application Ser. No. 61/296,050 filed Jan. 19, 2010 incorporated in its entirely by reference.

The invention relates to a process for preparing isocyanates by thermal dissociation of carbamates, also known as carbamic esters or urethanes.

Dissociation of carbamates is becoming increasingly important as a phosgene-free process for preparing isocyanates. Various apparatuses have been proposed for carrying out the dissociation of carbamates industrially, in particular columns (in EP 0 795 543), fluidized-bed reactors (in EP 555 628 and DE 199 07 648), falling film or thin film evaporators (in EP 0 092 738). The dissociation of carbamates can be carried out in the liquid phase or in the gas phase.

A problem in the thermal dissociation of carbamates is the formation of high molecular weight by-products which are formed by further reaction of the dissociation products with themselves or with the starting materials. These can lead to deposits in the apparatuses and thus restrict continuous operation and lead to decreases in yield. The residues comprise, in particular, allophanates and isocyanurates. The by-products are formed by reaction of monourethanes (semicarbamates, i.e. bifunctional compounds comprising a urethane function and an isocyanate function, intermediates in the dissociation of bisurethanes) with themselves.

To avoid these problems, the dissociation products isocyanate and alcohol in the carbamate dissociation gas have to be separated from one another as quickly as possible.

It is also known that the problems of backreaction and further reactions during the course of the dissociation is reduced by carrying out the carbamate dissociation in the presence of solvents since the reaction rate of the backreaction of isocyanate and alcohol (urethanization) and also of the further reactions are known to be dependent on the type of solvent and the dilution by the solvent. For example, J. H. Saunders and K. C. Frisch: Polyurethanes, Chemistry and Technology, 1962, p. 146, Table 10, gives information about the reactivity of isocyanates with alcohols in the presence of various solvents.

Dilution of the carbamate dissociation products with an inert solvent suppresses the formation of high molecular weight subsequent products; at the same time, the solvent serves to remove the secondary components and fouling of the apparatuses is reduced.

EP-B 0 795 543 describes particularly suitable solvents for the thermal dissociation of carbamates, which solvents have a defined boiling point or else a narrow boiling range and are obtained as distillation fraction of thermally stable liquids and are selected from the group consisting of the ortho, meta and para isomers of phenoxybiphenyl. The use of such solvents in the thermal dissociation of carbamates in columns enables the temperature at the bottom of the column to be reduced at the same dissociation performance and an unchanged average temperature in the reaction section, as a result of which the formation of by-products and cracking products in the liquid phase of the column is significantly reduced. Disadvantages of this process are that the runback at the top of the column comprises largely alcohol and that phenoxybiphenyl is difficult to obtain commercially and is therefore expensive.

It is also known that the rate of urethane formation can be reduced by addition of inhibitors. Inhibitors for urethane formation are, for example, hydrochloric acid, benzoyl chloride or p-toluenesulfonic acid (cf. Örtel: Polyurethane, 2nd edition, 3.4.2, p. 92).

In light of the above, it was an object of the invention to provide a process for preparing aromatic or aliphatic isocyanates by thermal dissociation of the corresponding carbamates, which makes high yields and a low proportion of by-products with little fouling possible.

The object is achieved by a process for preparing isocyanates by thermal dissociation of carbamates and separation by distillation of the reaction mixture from the carbamate dissociation, comprising the corresponding isocyanate and the corresponding alcohol, by distillation in a column having an enrichment section and a stripping section, where the carbamate is introduced between the enrichment section and the stripping section and the isocyanate is taken off as a constituent of the bottom stream and the alcohol is taken off as a constituent of the overhead stream from the column, in the presence of an inert solvent, wherein an intermediate boiler having a boiling point between the boiling point of the isocyanate and the boiling point of the alcohol under the operating conditions of the carbamate dissociation is used as inert solvent and is fed as external runback in liquid form in a purity of >95% by weight, based on the total weight of the external runback, in the upper region of the enrichment section and as gaseous, superheated stream into the stripping section at one or more points.

The addition of inert solvents for diluting the carbamate dissociation gas and thus reducing the formation of secondary components is known. Inert means, as usual, that the solvent does not react with the components of the reaction mixture under process conditions.

It has been found that the addition of an inert solvent which is an intermediate boiler, i.e. has a boiling point between the boiling point of the isocyanate and the boiling point of the alcohol under operating conditions, and is also used in high purity, i.e. in a purity of >95% by weight, makes it possible to obtain the alcohol corresponding to the carbamate in high purity at the top of the column without the runback comprising alcohol. As a result of the presence of alcohol in the liquid runback in the column being reduced or ruled out, the backreaction of the dissociation products to form the carbamate in the enrichment section is slowed. If, on the other hand, the runback were to be produced by pure alcohol, the enrichment section would have increased concentrations of alcohol. However, to achieve a maximum shift of the equilibrium in the direction of the dissociation products isocyanate and alcohol, the alcohol has to be removed from the system as quickly as possible. Furthermore, it is therefore advantageous to use low-pressure-drop high-performance packings having a holdup of less than 5% of the empty tube volume in the enrichment section in order to slow the reaction.

Predominantly carbamate dissociation occurs in the stripping section of the column.

The reaction is strongly endothermic. It has to be carried out in a short residence time with very little backmixing.

If the dissociation temperature selected is very high, for example above 300° C., the stripping section can comprise one or more falling film evaporators connected in series. However, if the dissociation temperature is lower, for example below 300° C., preference is given to using residence trays in order to achieve the target conversion.

The stripping section of the column in which the carbamate dissociation is carried out is therefore preferably configured as a falling film evaporator or as residence trays.

As residence trays, it is possible to select, for example, tunnel trays, Thormann trays or Lord trays, preferably Lord trays, for example as described in EP1493475B1. The trays can also be heated from below by means of steam in order to provide additional energy for the endothermic reaction.

The stripping section is preferably dimensioned so that the desired degree of carbamate dissociation, generally more than 99% of the carbamate used, is achieved at the bottom vaporizer.

To increase the resonance time, a sequence of falling film evaporators with redistribution via a distributor to the next falling film evaporator is also possible.

The one or more falling film evaporators connected in series or the residence trays can advantageously be catalytically coated.

If residence trays or in particular Lord trays are used, an immobilized heterogeneous catalyst or a suspended catalyst can be used on the trays.

The carbamate dissociation is, in particular, carried out at a temperature in the range from 210° C. to 400° C.

In the process of the invention, it is possible to use customary carbamates (also referred to as carbamic esters or urethanes), preferably biscarbamates, for the dissociation. These carbamates are usually based on the generally known reaction of amines, preferably diamines or polyamines, more preferably diamines, with urea and at least one alcohol.

The reaction of diamines or polyamines with carbonates to form the corresponding carbamate is particularly preferably carried out in the presence of alkoxides as base, as described in WO 2009/115538.

Suitable alcohols for preparing the carbamates are in principle all aliphatic alcohols. Preference is given to selecting alcohols whose boiling points differ sufficiently from the boiling point of the isocyanates to ensure optimal separation. Particular preference is given to using aliphatic monohydroxy alcohols having from 1 to 4 carbon atoms per molecule, i.e. methanol, ethanol, propanol, isopropanol, n-butanol and/or isobutanol, for preparing the carbamate. Preference is also given to alcohols having at least one oxygen heteroatom, in particular 2-methoxyethanol, 2-ethoxyethanol, 2-propoxyethanol, 2-butoxyethanol, 2-methoxy-1-propanol and/or 1-methoxy-2-propanol.

As amines, preference is given to using 2,4- and/or 2,6-toluenediamine (TDA), 2,2'-, 2,4'- and/or 4,4'-diaminodiphenylmethane (MDA) and/or higher homologues (poly-phenylenepolymethylenepolyamines, pMDA), 1,6-hexamethylenediamine (HDA), 1-amino-3,3,5-trimethyl-5-aminomethylcyclohexane (hereinafter also referred to as isophoronediamine, IPDA), 1,5- and/or 1,8-diaminonaphthaline, 4,4'-diaminodiphenyl, 1,3- and/or 1,4-diaminobenzene, 2,4- and/or 2,6-hexahydrotoluenediamine and/or 4,4'-, 2,4'- and/or 2,2'-dicyclohexylmethanediamine. The structures of the amines used determine the structures of the isocyanates which can be obtained after the thermal dissociation. The urethanes used are particularly preferably based on 2,4- and/or 2,6-toluenediamine (TDA), 2,2'-, 2,4'- and/or 4,4'-diaminodiphenylmethane (MDA) and/or higher homologues (polyphenylenepolymethylenepolyamines, pMDA), 1,6-hexamethylenediamine (HDA), isophoronediamine (IPDA) and/or 1,5-diaminonaphthaline as amine component and methanol, n-propanol, isopropanol, n-butanol, or in particular isobutanol or 2-methoxyethanol as alcohol.

Accordingly, particular preference is given to using the following diurethanes or polyurethanes for the dissociation: 2,4- and/or 2,6-toluenediisobutylurethane, 2,4- and/or 2,6-toluenedimethoxyethylurethane, 2,4- and/or 2,6-toluenedipropylurethane, 2,4- and/or 2,6-toluenedimethylurethane, 1,5-naphthalenediisobutylurethane, 1,5-naphthalenedimethoxyethylurethane, 1,5-naphthalenedipropylurethane, 1,5-naphthalenedimethylurethane, 4,4'-, 2,4'- and/or 2,2'-diphenylmethanediisobutylurethane, 4,4'-, 2,4'- and/or 2,2'-diphenylmethanedimethoxyethylurethane, 2,4'- and/or 2,2'-diphenylmethanedipropylurethane, 4,4'-, 2,4'- and/or 2,2'-diphenylmethane-dimethylurethane, polyphenylenepolymethylenepolymethoxyethylurethane, poly-phenylenepolymethylenepolymethylurethane, polyphenylenepolymethylenepolypropylurethane, polyphenylenepolymethylenepolyisobutylurethane, 1,6-hexamethylenediisobutylurethane, 1,6-hexamethylenedmethoxyethylurethane, 1,6-hexamethylenedipropylurethane, 1,6-hexamethylenedimethylurethane, isophoronediisobutylurethane, isophoronedimethoxyethylurethane, isophoronedipropylurethane and/or isophoronedimethylurethane, with mixtures of the urethanes mentioned also being able to be used for the dissociation.

Particular preference is given to preparing the following isocyanates by thermal dissociation of the corresponding diurethanes: tolylene 2,4- and/or 2,6-diisocyanate (TDI), 2,2'-, 2,4'- and/or 4,4'-diisocyanatodiphenylmethane (MDI), polyphenylenepolymethylene polyisocyanate (pMDI), hexamethylene 1,6-diisocyanate (HDI), 1-amino-3,3,5-trimethyl-5-aminomethylcyclohexane (isophorone diisocanate, IPDI) and/or 1,5-diisocyanatonaphthalene (NDI).

As inert solvent, preference is given to using a solvent which has a boiling point in the range from 70 to 350° C. under normal conditions.

The inert solvent is particularly preferably an intermediate boiler having a boiling point in the range from 100° C. to 250° C.

Suitable inert solvents are, in particular, tetralin, diphyl (mixture of biphenyl and diphenyl ether), biphenyl, diphenyl ether, the isomeric benzyltoluenes, the isomeric dibenzyltoluenes, dibenzyl ether, the isomeric trichlorobenzenes, the isomeric dichlorotoluenes, the isomeric diethyltoluenes, the isomeric diethylbenzenes, the isomeric dipropylbenzenes, the isomeric diisopropylbenzenes and/or the isomeric tetramethylbenzenes.

In a preferred embodiment, inert solvent is additionally introduced at the feed point for the carbamate which is fed to the dissociation. The solvent can be introduced in liquid, dewy (just totally vaporized) or preferably a gaseous form.

This is particularly preferably the same solvent which is fed in liquid form as external runback to the enrichment section and as gaseous, superheated stream in the lower region of the stripping section. In addition, dewy or superheated steam can be introduced at a plurality of points into the stripping section of the column.

The vapor taken off from the enrichment section is advantageously quenched.

According to the invention, it is also important that the quenched vapor does not consist of pure alcohol but instead comprises from 10 to 95% by volume of solvent, preferably from 50 to 95% by volume of solvent.

The invention is illustrated below with the aid of a drawing and examples.

FIG. 1 schematically shows a plant for carrying out the process of the invention.

A stream 1 of the carbamate to be dissociated is fed into the middle region of a column K having an enrichment section V and a stripping section A.

A stream 2 comprising the corresponding isocyanate is taken off from the bottom of the stripping section A and a stream 3 comprising the corresponding alcohol is taken off at the top of the enrichment section V.

In the upper region of the enrichment section V, a stream 4 comprising an intermediate boiler having a boiling point between the boiling point of the isocyanate taken off at the bottom and the boiling point of the alcohol taken off at the top and having a purity of >95% is introduced in liquid form.

In the lower region of the stripping section A, a stream 5 comprising the gaseous, superheated intermediate boiler is introduced.

In the preferred embodiment shown in the FIGURE, a stream of the same intermediate boiler, stream 6, is additionally introduced together with the carbamate to be dissociated, stream 1, into the middle region of the column K.

EXAMPLES

Example 1a

Dissociation Above 300° C. (According to the Invention)

A dissociation apparatus as shown in FIG. 1 is used. The apparatus has six theoretical plates in the enrichment section V and one theoretical plate in the stripping section A. This stripping section A comprises an upright bundle of tubes.

2.5 kg/h of a 20% strength by weight solution of tolylene 2,4-bis(O-diisobutylcarbamate) (stream 1) in 1,2,4-trichlorobenzene are fed at 120° C. into the dissociation apparatus above the stripping section.

The column is operated at a pressure of 10 bar. 1.0 kg/h of 1,2,4-trichlorobenzene boiling at 339° C./10 bar (stream 6) are additionally introduced at the feed point of the column. At the top of the column, 2.3 kg/h of 1,2,4-trichlorobenzene (stream 4) having a purity of 99.5% are fed at 300° C. onto the liquid distributor. The temperature at the bottom is 348° C. At the bottom of the column, 0.053 kg/h of N, (stream 5) and 0.4 kg/h of 1,2,4-trichlorobenzene vapor (350° C.) are introduced in order to strip out the alcohol. Out of the bottom outlet of the column, 3.6 kg/h of a mixture (stream 2) comprising 248 g/h of tolylene 2,4-diisocyanate (TDI), 149 ppm of semicarbamates and 23.3 g/h of high-boiling secondary components are taken off. The 1,2,4-trichlorobenzene content is 92.4%.

At the top of the apparatus, 2.66 kg/h of a mixture comprising 8.3% by weight of isobutanol and 0.1% by weight of 2,4-TDI and less than 100 ppm of semicarbamates are taken off at 318° C.

The 1,2,4-trichlorobenzene fed in at two points (streams 6, 4) has the same composition in each case (purity: 99.5%).

The total yield of 2,4-TDI in the overhead product and the bottom product is 92.9%.

Example 1b

Dissociation Above 300° C. (for Comparison)

A dissociation apparatus as shown in FIG. 1 is used. The apparatus has six theoretical plates in the enrichment section V and one theoretical plate in the stripping section A. This stripping section A comprises an upright bundle of tubes.

2.5 kg/h of a 20% strength by weight solution of tolylene 2,4-bis(O-diisobutylcarbamate) (stream 1) in 1,2,4-trichlorobenzene are fed at 120° C. into the dissociation apparatus above the stripping section.

The column is operated at a pressure of 10 bar. 1.0 kg/h of 1,2,4-trichlorobenzene boiling at 339° C./10 bar (stream 6) are additionally introduced at the feed point of the column. However, no 1,2,4-trichlorobenzene is added at the top of the column, but instead a condenser is operated at a reflux ratio of 0.8. The temperature at the bottom is 348° C. At the bottom of the column, 0.12 kg/h of $N_2$ (stream 5) and 0.4 kg/h of 1,2,4-trichlorobenzene (350° C.) are introduced in order to strip out the alcohol. Out of the bottom outlet of the column, 2.3 kg/h of a mixture (stream 2) comprising 214 g/h of 2,4-TDI, 15 ppm of semicarbamates and 34.5 g/h of high-boiling secondary components are taken off. The 1,2,4-trichlorobenzene content is 89.2%.

At the top of the apparatus, 1.71 kg/h of a mixture comprising 12.9% by weight of isobutanol and 1.7% by weight of 2,4-TDI and less than 100 ppm of semicarbamates are taken off at 296° C. The total yield of 2,4-TDI in the bottoms and overhead stream is only 89.5%.

Example 2

Dissociation Below 300° C. (According to the Invention)

A dissociation apparatus as described in FIG. 1 is used. The apparatus has ten theoretical plates in the enrichment section V and 30 theoretical plates in the stripping section A. The stripping section has no dedicated vaporizer. The apparatus has low-pressure-drop woven packings having a holdup of less than 5%, based on the empty tube cross section, in the enrichment section. The stripping section comprises 30 residence trays as described in EP 1493475 B1.

1.0 kg/h of a 50% strength by weight solution of tolylene 2,4-bis(O-diisobutylcarbamate) (stream 1) in 1,2,4-trichlorobenzene are introduced at 180° C. into the dissociation apparatus above the stripping section (a plate 30 from the bottom).

The column is operated at a pressure of 4 bar. 2.37 kg/h of gaseous 1,2,4-trichlorobenzene superheated to 281° C. (stream 6) are additionally introduced at the feed point of the column (plate 30 from the bottom). Furthermore, 0.49 kg/h of superheated 1,2,4-trichlorobenzene is introduced at 281° C. at plate 15 from the bottom. At the top of the column, 0.95 kg/h of 1,2,4-trichlorobenzene (stream 4) having a purity of 99.5% is fed at 250° C. onto the liquid distributor. The temperature at the bottom is 270° C. At the bottom of the column, 0.03 kg/h of $N_2$ (stream 5) for stripping out the alcohol and 1.17 kg/h of gaseous 1,2,4-trichlorobenzene at 281° C. to introduce energy are fed in. At the bottom outlet of the column, 3.8 kg/h of a mixture (stream 2) comprising 5.1% by weight of 2,4-TDI are taken off.

At the top of the apparatus, 2.0 kg/h of a mixture comprising 9.2% by weight of isobutanol and 0.05% by weight of 2,4-TDI and less than 100 ppm of semicarbamates are taken off at 264° C.

The 1,2,4-trichlorobenzene fed in at four points (runback, stream 6, plate 15, bottom) has the same composition in each case (purity: 99.5%).

In this preferred embodiment, neither vaporizers nor condensers are used. Fouling of a heat exchanger in the dissociation apparatus is thus ruled out.

The invention claimed is:

1. A process for preparing an isocyanate, the process comprising:

thermally dissociating a carbamate in a column in the presence of an inert solvent, to obtain an isocyanate and an alcohol, and separating the isocyanate and the alcohol by distillation, to obtain a bottom stream comprising the isocyanate and an overhead stream comprising the alcohol and the inert solvent, wherein the inert solvent is an intermediate boiler having a boiling point between the boiling point of the isocyanate and the boiling point of the alcohol under the operating conditions of the carbamate dissociation, wherein the column comprises an enrichment section, a feed point, and a stripping section, the feed point being disposed between the enrichment section and the stripping section, and wherein the column is configured, and the process is conducted such that:

the carbamate is introduced into the column in the feed point;

the inert solvent is introduced into one or more points on the stripping section as gaseous, superheated stream;

the isocyanate is removed as a constituent of the bottom stream from the bottom of the stripping section;

the alcohol is removed as a constituent of the overhead stream from the top of the enrichment section; and inert solvent from the overhead stream is partially or completely introduced into an upper region of the enrichment section of the column as an external runback in liquid form having a purity of >95% by weight, based on the total weight of the external runback.

2. The process of claim 1, wherein the inert solvent has a boiling point in the range from 70 to 350° C. under atmospheric pressure.

3. The process of claim 2, wherein the inert solvent has a boiling point in the range from 100 to 250° C.

4. The process of claim 3, wherein the alcohol is an aliphatic monohydroxy alcohol.

5. The process of claim 1, wherein the stripping section of the column is configured as a falling film evaporator.

6. The process of claim 5, wherein the stripping section of the column comprises a plurality of falling film evaporators connected in series with distributors arranged in between.

7. The process of claim 5, wherein the falling film evaporator is catalytically coated.

8. The process of claim 1, further comprising introducing a stream of an inert solvent into the column at the feed point.

9. The process of claim 8, wherein the stream of the inert solvent introduced into the column at the feed point comprises the same inert solvent which is fed as intermediate boiler as external runback to the upper region of the enrichment section and as gaseous, superheated stream into the stripping section.

10. The process of claim 1, wherein the overhead stream comprising the alcohol is taken off in gaseous form and is quenched immediately after being taken off.

11. The process of claim 1, wherein from 50 to 100% of the isocyanate formed in the dissociation of the carbamates is taken off via the bottom of the stripping section.

12. The process of claim 1, wherein the dissociation of the carbamate is carried out at an operating temperature in the range from 210° C. to 400° C.

13. The process of claim 1, wherein the stripping section of the column comprises residence trays, which are Lord trays.

14. The process of claim 13, wherein the residence trays comprise a catalyst.

15. The process of claim 3, wherein the alcohol is methanol, butanol, isobutanol, methoxyethanol, butoxyethanol, or 2-methoxy-1-propanol.

16. The process of claim 6, wherein the falling film evaporators connected in series are catalytically coated.

* * * * *